United States Patent [19]

Preston, Jr.

[11] Patent Number: 4,777,525

[45] Date of Patent: Oct. 11, 1988

[54] APPARATUS AND METHOD FOR A MULTI-RESOLUTION ELECTRO-OPTICAL IMAGING, DISPLAY AND STORAGE/RETRIEVAL SYSTEM

[76] Inventor: Kendall Preston, Jr., 4701 E. Glenn St., Bldg. 36, Tucson, Ariz.

[21] Appl. No.: 812,657

[22] Filed: Dec. 23, 1985

[51] Int. Cl.$^4$ .............................................. H04N 7/18
[52] U.S. Cl. ....................... 358/102; 358/93; 358/225; 358/287; 350/171
[58] Field of Search ............... 358/93, 102, 903, 209, 358/225, 106, 107, 287, 22, 213, 288, 212; 350/254, 171; 382/8; 354/79, 110, 159; 364/525, 526; 340/720, 723, 731

[56] References Cited

U.S. PATENT DOCUMENTS

| | | | |
|---|---|---|---|
| 3,772,516 | 11/1973 | Roberts et al. | 358/125 X |
| 3,895,854 | 7/1975 | Ziffer | 350/171 X |
| 3,978,280 | 8/1976 | Kavanagh et al. | 358/93 |
| 4,009,942 | 3/1977 | Hirose | 350/171 X |
| 4,061,914 | 12/1977 | Green | 356/39 X |
| 4,160,263 | 7/1979 | Christy et al. | 358/93 X |
| 4,168,512 | 9/1979 | Ito et al. | 358/93 X |
| 4,385,317 | 5/1983 | Furuya et al. | 358/93 |
| 4,506,300 | 3/1985 | Fearnside | 358/102 X |
| 4,555,798 | 11/1985 | Broadbent, Jr. | 358/107 X |
| 4,589,140 | 5/1986 | Bishop et al. | 358/106 X |
| 4,614,966 | 9/1986 | Yunoki et al. | 358/212 X |
| 4,633,306 | 12/1986 | Utsugi | 358/102 |
| 4,634,882 | 1/1987 | Craine et al. | 358/212 X |
| 4,641,198 | 2/1987 | Ohta et al. | 358/287 X |
| 4,672,559 | 6/1987 | Jansson et al. | 358/93 X |
| 4,673,972 | 6/1987 | Yokomizo | 358/287 X |
| 4,673,988 | 6/1987 | Jansson et al. | 358/287 X |

FOREIGN PATENT DOCUMENTS 0100425  6/1984  Japan ........................ 354/159

Primary Examiner—Howard W. Britton
Assistant Examiner—Victor R. Kostak
Attorney, Agent, or Firm—Harry M Weiss & Associates

[57] ABSTRACT

An electro-optical scanning, display, and storage/retrieval system and method are described for examination of a specimen under a plurality of magnifications. A low resolution image can be provided by moving a specimen past one or more sets of radiation sensitive arrays. Three methods can be employed for providing this low resolution image; (1) by using red, green and blue sensing arrays, (2) by means of RGB filters, and (3) by sequentially illuminating a single array with red, blue and green light. Output signals involving each color component are properly coordinated so as to reconstruct the image of the specimen. Subsequently, the specimen is optically imaged at a multiplicity of higher magnifications generating images which are spatially correlated with the low resolution image. Three methods are described for providig this plurality of magnifications. These include a zoom lens system, a system employing a plurality of optical paths with different magnification for each color component, and use of high resolution image detection system wherein the low resolution image is produced by digitally converting image data from stored high resolution information. The multi-resolution images can be transformed into digital signals that can provide for convenient archival and retrieval of the images.

19 Claims, 3 Drawing Sheets

APPARATUS AND METHOD FOR A MULTI-RESOLUTION ELECTRO-OPTICAL IMAGING, DISPLAY AND STORAGE/RETRIEVAL SYSTEM

BACKGROUND OF THE INVENTION

1. Field of the Invention

This invention relates generally to electro-optical scanning systems and, more particularly, to scanning systems that involve indirect viewing (via a television intermediary) of an image field at a plurality of magnifications.

2. Discussion of the Related Art

Automatic systems for scanning and analyzing microscope field images have been developed, the most notable being the automatic scanning and examination of blood cells. However, the interpretive ability of visual examination by a human observer is still generally required for accurate analysis, particularly with respect to, for example, histological specimens. Typical microscopic examination of a specimen involves the examination of the specimen by direct viewing through oculars using various objective elements to provide a plurality of magnifications. Different magnifications can be accomplished by selectively positioning the various objective lenses located in a turret immediately over the specimen. By rotation of the turret, objective lenses of different magnifications can be used to examine the specimen. The general procedure is to scan a specimen at relatively low magnification and then to use higher magnification to examine selected specimen areas in detail.

The direct viewing process, through widely utilized, has several disadvantages. First, the microscope field images at a plurality of magnifications cannot be viewed simultaneously. In addition, the manual positioning of the turret containing the plurality of lenses frequently makes more detailed examination of a selected specimen region ambiguous because of the lack of knowledge of the precise spatial relationship between the fields viewed at different magnifications. Furthermore, viewing of a specimen through an ocular for a long period of time can be tiring. Finally, photography and storage of images can require a separate operation, frequently disturbing the examination routine.

Similar problems can be found in examination of images recorded on high-resolution photographic emulsions such as those used in aerial photography and in the storage of documents on microfiche. Typically, a search for certain selected information is conducted at relatively low magnification. Examination of areas of the low magnification image in which the selected information may be present can then be performed at a higher magnification until the presence of the selected information is confirmed or rejected.

A need has therefore been felt for a microscope scanning system that can view and present to the user images of a specimen under a plurality of magnifications simultaneously, can accurately determine spatial the relationships between the plurality of images and can conveniently store and retrieve the images for future examination and for comparison purposes.

SUMMARY OF THE INVENTION

It is therefore an object of the present invention to provide an improved optical scanning system.

It is another object of the present invention to provide an optical scanning system that does not require direct viewing through oculars by the user.

It is yet a further object of the present invention to provide an optical scanning system that can not only provide a viewer with images of a specimen region at a plurality of magnifications simultaneously, but also does not require direct viewing by the user.

It is a more particular object of the present invention to provide an array of photodetectors that can create a low magnification image of the specimen as a whole when the specimen is loaded into the multi-resolution scanning system.

It is yet another particular object of the present invention to provide an apparatus and method for viewing an image at a plurality of locations of the specimen.

It is yet another object of the present invention to provide an optical scanning system capable of displaying images of a selected specimen region at a plurality of magnifications simultaneously.

It is yet another objective of the present invention to provide for storage and for retrieval of the images of the specimen.

These and other objects are accomplished, according to the present invention, by an optical scanning system in which, when a specimen is loaded, it is illuminated and conveyed before one or more arrays of photosensitive elements. The motion of the specimen past the photosensitive elements provides electrical signals from which a low magnification image, an image capable of being digitally processed, can be stored and electronically displayed. The electrical signals can be generated by separate red, green and blue photosensitive elements or by a single photosensitive array element in combination with appropriate filter elements. Alternatively, when a single photosensitive array is utilized, it can be sequentially illuminated by red, green and blue light during the loading interval in order to obtain a composite color image. The specimen can then be positioned so that higher magnification images can be applied to other photosensitive devices. The position of these images can be spatially correlated with the low resolution image previously acquired. The images at the plurality of higher magnifications can be simultaneously displayed on a plurality of video monitors with the low resolution image, or the higher magnification images can be displayed separately on a single video monitor. The plurality of higher magnifications can be achieved by either a zoom lens element, a multiplicity of imaging systems for various magnifications, or the use of a high resolution array of detecting elements addressed in such a fashion that the resolution is electronically modified so as to produce both high, low, and medium resolution images. Finally, any one of the images may be stored archivally in digital form for future recall.

These and other features of the present invention will be understood upon reading of the following description along with the observation of the figures.

DESCRIPTION OF THE PREFERRED EMBODIMENT

Detailed Description of the Figures

Figure 1A:
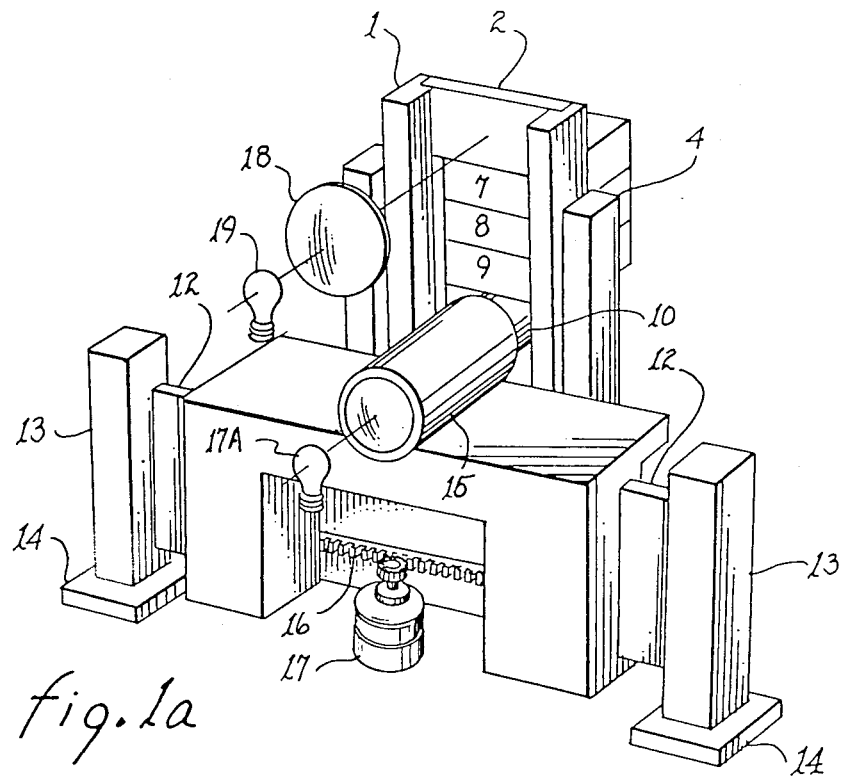
FIGS. 1a and 1b are perspective views of apparatus for generating a signal representation of a shadow image and for providing a magnified image of a scanning area thereon in accordance with the present invention.
Figure 1B:
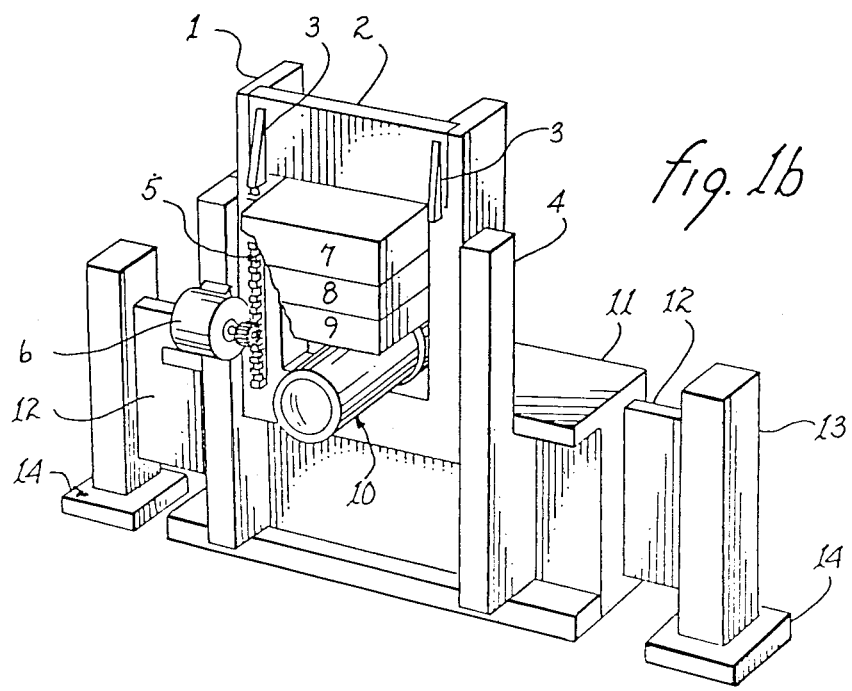

Referring to FIG. 1a and 1b, a substrate 2 carrying, for example, a histological specimen (mounted on a microscope slide) or a high-resolution photographic emulsion mounted on an appropriate substrate, is held by clips 3 in traverse member 1 and associated apparatus which position and control the motion of the specimen 2. When placing the specimen 2 into the traverse member 1, the traverse member 1 is moved by motor 6 and associated gears coupled to gear rack 5 so that the specimen moves past three line-scan diode-array sensors 7, 8 and 9. A lamp 18 and a collimating lens 19 provide generally parallel light to the line-scan diode arrays as the slide is moved past these sensors. The signals from the sensors are digitized and the three separate color images are provided with proper registration so that a full image can be reconstructed and displayed from the three sets of output signals. The full color image is referred to hereinafter as a shadow image. It should be understood that a lens system is not used in producing the shadow image. The shadow image is of a larger area than attainable with a lens system. The specimen 2 is then positioned by traverse member 1 and associated apparatus so that radiation from lamp 17A passing through condensing lens 15 illuminates the specimen. An image of the specimen is relayed by objective lens 10 to a plurality of optical detectors (not shown in these figures). The optical detectors are adapted to receive a plurality of magnified images of a scanning area of the specimen. The specimen 2 can be moved relative to the optical detectors by motors 17 and 6 along with the associated gears coupled to gear racks 5 and 16 respectively. These motors, gears and associated gear racks can control the position of the specimen 2 horizontally and vertically by positioning traverse member 4 relative to support member 11 and by positioning traverse member 1 relative to traverse member 4, respectively. Focusing can be accomplished, in part, by movement of support member 11 in a direction parallel to the optical axis using flexure mount 12 supported by post 13 coupled to an optical bench (not shown) by mount 14.

Figure 2:
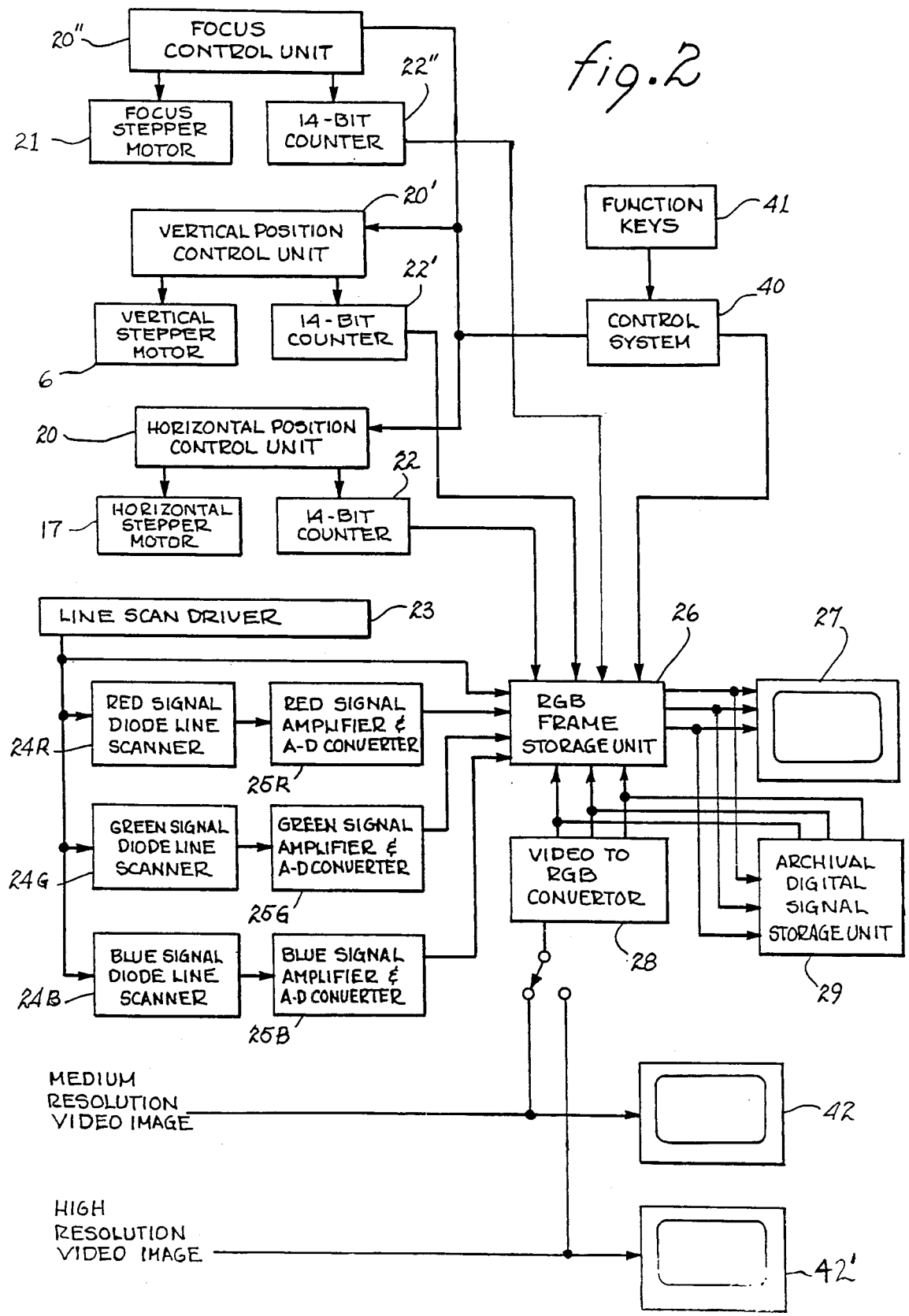
FIG. 2 is a block diagram of the preferred embodiment of the present invention.

Referring next to FIG. 2, a block diagram of the control system, image generation system, image display system and image storage/retrieval system of the apparatus for FIG. 1 is shown. For the photosensitive arrays or diode line scanners, 24R(ed), 24G(reen) and 24B(lue), a synchronous line scan driver 23 ensures that the images resulting from activation of the photosensitive arrays can be aligned horizontally with the proper spatial relationship while pulses to the vertical motor 6 as recorded by 14 bit-counter 22' and the known separation between the diode line scanners provide vertical alignment. The red, green and blue diode line scanners provide output signals that are amplified and converted to digital signals in units 25r, 25g and 25b. A Red-Green-Blue (RGB) frame storage unit 26 can be used to acquire and align these low resolution images and the resultant full-color shadow image can be displayed on the RGB display unit 27.

In order to acquire higher resolution images of a scanning area of the specimen, optical magnifying systems, such as are described with reference to FIG. 3a, FIG. 3b and FIG. 3c can be used. The magnified image is focused on a photodetecting device, such as a vidicon. The internal photodetector scan control (not shown in these figures) controls the photosensors scanning each color. The internal camera scan control can apply these images either to a plurality of instantaneous displays 42 and 42' or to a video to RGB converter 28 for storage in the RGB frame storage unit 26 for display on RGB display unit 27. Shadow images from line scanners 24R, 24G and 24B and the higher resolution images can be transferred to an archival signal storage unit 29 for later retrieval. Vertical and horizontal position control units, 20 and 20', respectively, and horizontal and vertical stepping motors, 17 and 6, respectively, can control the viewing location of the scanning area. Counters, 22 and 22', respectively, can be used to determine the location of the scanning area on the shadow image. The focus control unit 20" and focus stepping motor 21 (not shown in FIG. 1) control the focus of the image of the scanning area by deflection of the flexure mount 12 shown in FIG. 1. The vertical control, horizontal control and focus control are governed by a central control system 40, that can respond to input signals from, for example, function keys 41. These function keys can also be used to control transfer of images to and from the RGB store, the low and high magnification scanners, and the image storage and retrieval unit. Function keys can also control a cursor on display unit 27 for the shadow image permitting the identification thereon of the scanning area. The function keys provide signals that are processed by the control system 40 and result in appropriate signals being applied to the controlled apparatus. The control system 40 is preferably a microprocessor which has the function keys 41 programmed to move the specimen to any desired position. The contents of the 14-Bit Counters 22, 22', 22" are inputs, as shown in FIG. 2, (which are gated by the input from the control system 40) to the RGB Frame Storage Unit 26.

Figure 3A:
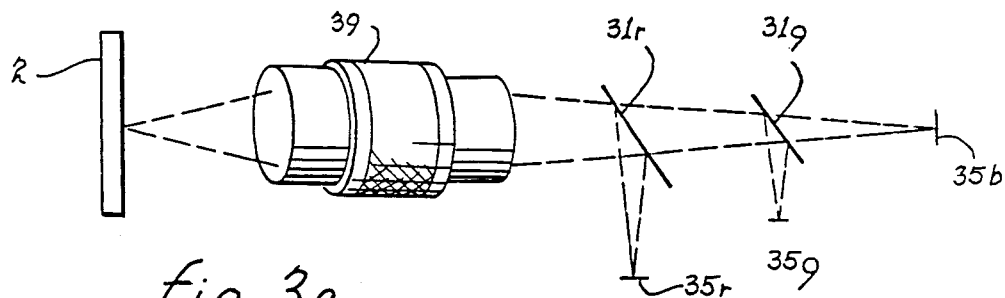
FIG. 3a is a partially pictorial schematic diagram of apparatus for providing a view, with a selectable resolution of the scanning area.

Referring now to FIG. 3a, a first mechanism for providing a plurality of magnifications is shown. light from specimen 2 is transmitted through a zoom lens optical system 39 to provide a variable controllable magnification. The light beam transmitted by the zoom lens system 39 is reflected off a dichroic filter 31r so that the red portion of the beam is imaged on photodetector 35r. A second dichroic filter reflects the remaining green components of the beam from the remaining light at dichroic filter 31g and this reflected light is imaged on photodetector 35g. The remaining blue component of the light is imaged on photodetector 35b. Each photodetector (35r, 35g and 35b) can be either a Charge-Coupled Device(CCD) array, vidicon or another type of light sensitive device. The outputs of these photodetectors provide the input to the video to RGB convertor 28. For each setting of the zoom lens, an image may be converted and stored in RGB storage unit 26, displayed by RGB monitor 27, and stored, if desired, in archival storage unit 29. Simultaneously the present image may be displayed on either monitor 42 or 42' thus providing the required multi-resolution display.

Figure 3B:
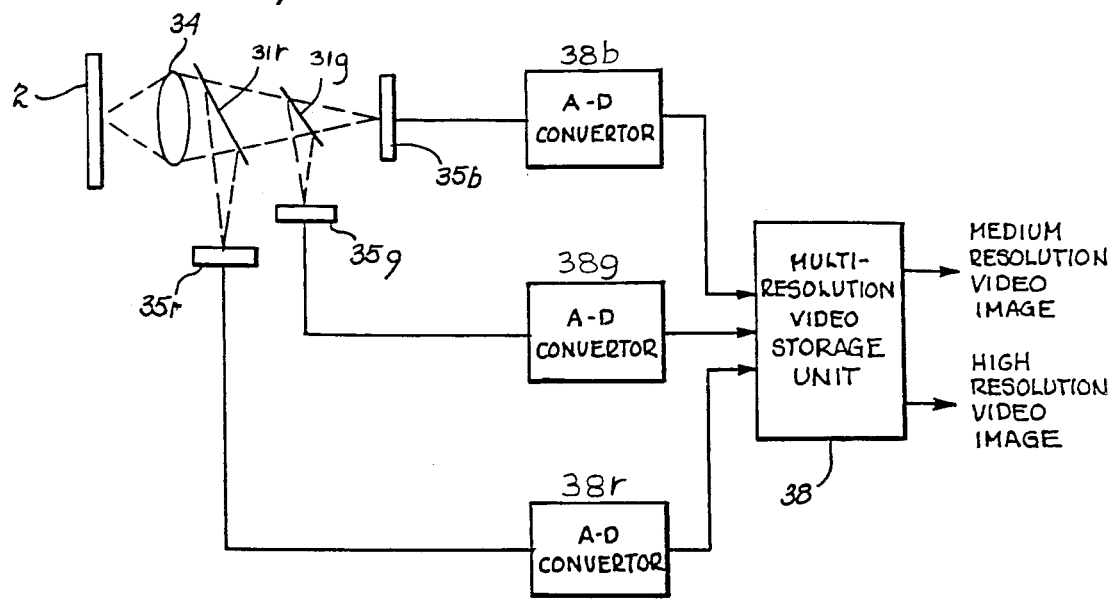
FIG. 3b is a schematic block diagram of apparatus for generating and storing a signal representation of the image of the scanning area.

Referring next to FIG. 3b, another method of providing images at a plurality of magnification is shown. The light which illuminates specimen 2 and is focused by lens system 34 to generate an optical image. A portion of the beam containing the red light is reflected from dichroic mirror 31r onto photodetecting array 35r, while a second portion of light containing the gree information is reflected from dichroic filter 31g onto photodetector 35g. The remaining portion of the beam containing the blue light is imaged on photodetector 35b. The output signals of the photodetecting arrays 35r, 35g and 35b are applied to analog-to-digital converters 38r, 38g and 38b, and thereafter stored in multi-resolution signal storage unit 38, wherein each color component has a separate storage region. A medium resolution image can be provided to display unit 42 (FIG. 2) by the address generator associated with storage unit 38, while a high resolution image can be provided to display 42' (FIG. 2) by a second address generator container in storage unit 38. The multi-resolution video storage unit 38 (see FIG. 3b) is used to simultaneously provide both a medium resolution video image and a high resolution video image. The medium resolution video image is produced by an address generator that takes a sub-sample of the entire image stored in multi-resolution video storage unit 38 whereas the high resolution video image is produced by an address generator which samples each point of a sub-region within the multi-resolution video storage unit 38. The arrays 35r, 35g and 35b, as well as the associated storage unit 38 contain the information for both the medium and the high resolution video images.

Figure 3C:
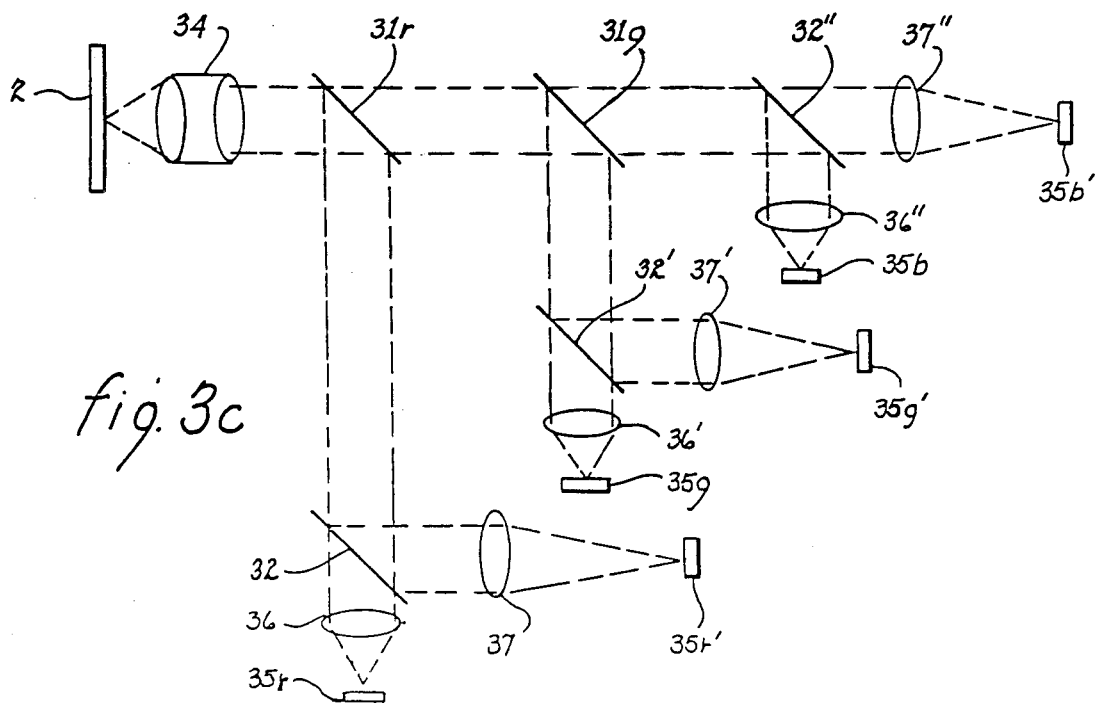

Referring next to FIG. 3c, a third apparatus and method for producing images with a plurality of magnifications is shown. The light which illuminates the specimen 2 is collimated by lens system 34. The portion of the beam containing the red light is reflected off dichroic filter 31r. The light reflected from this dichroic filter is passed through beam splitter 32 so that a portion of the light is imaged by a lens system 36 on photodetector 35r and the remaining portion of the light reflected by the beam splitter is imaged by lens system 37 on photodetector 35r'. The light passing directly through dichroic filter 31r has the green component reflected by dichroic filter 31g. The light reflected from dichroic filter 31g is passed through beam splitter 32' so that a portion of the light is imaged by a lens system 36' on photodetector 35g, while a second portion of the light is imaged by lens system 37' on photo detector 35g'. The light passing through filter 31g is passed through beam splitter 32". A portion of the light that is reflected is imaged by lens system 36" on photodetector array 35b while a second portion of the light passing through the beam splitter 32" is imaged by means of lens system 37" on a photodetector 35b'. The lenses 36, 36' and 36" and 37, 37' and 37" provide two magnifications so that medium and high resolution images can be produced simultaneously. Photodetectors 35r and 35r', 35g and 35g', 35b and 35b' provide, in combination, two simultaneously images at two different magnifications which are then transmitted to monitors 42 and 42'. These photodetectors can be CCD arrays or vidicons as is characteristic of television systems or other optical detection systems with suitable resolution.

Operation of the Preferred Embodiment

In the image viewing system of the instant invention, single magnification direct viewing of the specimen at a given time is not employed. Instead, images at a multiplicity of magnification, with regions at higher magnification located within the lower resolution image, can be viewed simultaneously or in sequence. Indeed, in the preferred embodiment, three images can be viewed simultaneously so that a comparison can be made of areas of interest at the different magnifications. In addition, the presence of the cursor or similar identifying electronically generated optical cue on the the monitor screen permits scanning by a higher resolution image of a lower resolution image to occur in a systematic manner. This scanning process avoids the loss of orientation typical of the direct-viewing, single-magnification microscope which occurs when the turret containing the various objective lenses are rotated from one position into another position. Because the information is digitized for viewing on the RGB monitors, this information is in a format that is also convenient for digital storage. Thus a plurality of regions of interest can be stored in the archival digital signal storage apparatus and withdrawn for simultaneous examination as desired. It will of course be clear that in attempting to find certain phenomena in a particular specimen, standard images of similar specimens can also be retrieved from the archival system for comparison purposes. Similarly it will be clear that the scanning of the specimen can be observed simultaneously at a plurality of viewing stations so that more than one investigator can provide his expertise during an examination.

Three methods of providing simultaneously medium and high resolution images are described. The greatest flexibility, of course, is obtained in FIG. 3b where, by simply sub-sampling the high resolution image formed by high resolution CCD arrays, a lower resolution image can be generated electronically without a plurality of additional optical channels. However, better image quality can be obtained from the arrangement of FIG. 3c because separate optical elements are provided for each resolution. The arrangement of FIG. 3a has the advantage of the simplicity of a single optical system but the disadvantage that simultaneous multi-resolution viewing is only obtainable using a separate frame store for each resolution.

In the preferred embodiment, the use of stepper motors 6, 17, 21 and associated counters 22, 22', 22" permit convenient correlation of the location of the higher resolution image with the position of marker signals on the lower resolution image indicating the location of the higher resolution image. The quantized movement of the stepper motor provides precise identification of a current image position.

The scanning system of the instant invention is particularly well suited for the analysis of histological specimens. In particular, the lower magnification images can be used as a guide to determine the region requiring inspection at higher magnification. However, it will be clear that the system can also be used for any image-bearing specimen such as a photographic emulsion.

The array of low resolution diode-sensors has been found to provide a resolution of approximately one thousandeth inch with readily available technology. The image produced by passing the specimen in front of the sensor array(s) can be digitally stored and displayed. By the procedures described above, the image developed from the low resolution sensor arrays can also be modified and images at various magnifications provided without the requirement for additional optical apparatus.

The above description is included to illustrate the operation of the preferred embodiment and is not meant to limit the scope of the invention. The scope of the invention is to be limited only by the following claims. From the above description, many variations will be apparent to one skilled in the art that would yet be encompassed by the spirit and scope of the invention.

What is claimed is:

1. A system for generating images of a specimen, comprising:
   means for generating a signal representation of a shadow image of said specimen;
   magnifying means for generating a signal representation of an image of a scanning area of said specimen;
   display means for providing simultaneous displays of said images; and
   means for identifying said scanning area on the display of said shadow image.

2. The system of claim 1 wherein said shadow image generating means includes an array of photosensitive diodes.

3. The system of claim 1 wherein said shadow image generating means comprises:
   a first array of photosensitive diode means for providing a signal representation of a red shadow image in response to a red component of light from said specimen;
   a second array of photosensitive diodes means for providing a signal representation of a green shadow image in response to a green component of light from said specimen;
   a third array of photosensitive diodes means for providing a signal representation of a blue shadow image in response to a blue component of light from said specimen; and
   means for storing signals provided by said array means.

4. The system of claim 8 wherein said display means provide a display of a full color shadow image in response to said stored signals.

5. The system of claim 1 wherein said magnifying means include a zoom lens system that receives light from said specimen, said zoom lens system being operable to provide a selected one of a multiplicity of magnifications.

6. The system of claim 5 wherein said magnifying means additionally comprises:
   a first dichroic filter disposed to receive light from said zoom lens system, received light of a first known color being reflected therefrom;
   a second dichroic filter disposed to receive light transmitted through said first dichroic filter, received light of a second known color being reflected therefrom;
   a third dichroic filter disposed to receive light transmitted through said second dichroic filter, received light of a third known color being reflected therefrom; and
   photodetector means for providing said signal representation of said image of said scanning area in response to light reflected from said dichroic filters.

7. The system of claim 6 wherein said photodetector means comprises first, second and third photodetector arrays disposed to receive light reflected from said first, second and third filters, respectively.

8. The system of claim 6 wherein said first, second and third known colors are red, green and blue, respectively.

9. The system of claim 6 wherein said photodetector means includes a charge-coupled device array.

10. The system of claim 6 wherein said photodetector means includes a vidicon.

11. The system of claim 1 wherein said magnifying means comprises:
    a lens system disposed at an object distance from said specimen;
    photodetector means for providing a signal representative of light transmitted thereto, said photodetector means being disposed at an image distance from said lens system; and
    filter means for transmitting light of a known color from said lens to said photodetector means.

12. The system of claim 11 additionally comprising an analog to digital converter connected to said photodetector means.

13. The system of claim 1 wherein said magnifying means includes means for generating a first signal representation of said image of said scanning area with a first magnification and a signal representation of said scanning area with a second magnification.

14. The system of claim 13 wherein said means for generating said first and second signal representation comprises:
    means for collimating light from said specimen;
    means for reflecting a portion of said collimated light of a known color;
    a beam splitter that splits said reflected light into first and second collimated beams;
    a first lens system that receives said first beam;
    a second lens system that receives said second beam;
    a first photodetector array disposed in the focal plane of said first lens system; and
    a second photodetector array disposed in the focal plane of said second lens system.

15. The system of claim 1 wherein said means for identifying includes means for displaying a cursor on said shadow image.

16. The system of claim 1 wherein said means for identifying comprises:
    a stepper motor operable to move said specimens;
    a counter connected to said stepper motor, the output of said counter being a coordinate of the location of said scanning area of said shadow image.

17. In a method of generating images of a specimen, the steps of:
    generating a signal representation of a shadow image of a specimen;
    generating a signal representation of an image of a scanning area of said specimen;
    providing a display of said images; and
    identifying said scanning area on the display of said shadow image.

18. The method of claim 17 additionally including the step of storing said signal representations.

19. The method of claim 17 wherein said step of generating signals representative of an image of scanning area includes generating first and second signals representations of said image of said scanning area with first and second magnifications, respectively.

* * * * *

UNITED STATES PATENT AND TRADEMARK OFFICE
CERTIFICATE OF CORRECTION

PATENT NO. : 4,777,525
DATED : Oct. 11, 1988
INVENTOR(S) : Kendall Preston, Jr.

It is certified that error appears in the above-identified patent and that said Letters Patent is hereby corrected as shown below:

In column 7, Claim 4, line 37, please change "claim 8" to --claim 3--.

Signed and Sealed this

Twenty-first Day of February, 1989

*Attest:*

DONALD J. QUIGG

*Attesting Officer*  *Commissioner of Patents and Trademarks*